United States Patent
Hollabaugh et al.

(10) Patent No.: US 10,241,015 B2
(45) Date of Patent: Mar. 26, 2019

(54) CRYOGENIC COOLING POSITIONING APPARATUS, METHODS AND APPLICATIONS

(71) Applicant: Mitegen, LLC, Ithaca, NY (US)

(72) Inventors: Stephen Hollabaugh, Ithaca, NY (US); Robert Newman, Groton, NY (US); David Closs, Freeville, NY (US)

(73) Assignee: Mitegen, LLC, Ithaca, NY (US)

( * ) Notice: Subject to any disclaimer, the term of this patent is extended or adjusted under 35 U.S.C. 154(b) by 86 days.

(21) Appl. No.: 15/657,988

(22) Filed: Jul. 24, 2017

(65) Prior Publication Data
US 2018/0024032 A1      Jan. 25, 2018

Related U.S. Application Data

(60) Provisional application No. 62/365,488, filed on Jul. 22, 2016.

(51) Int. Cl.
| | |
|---|---|
| *F16H 1/28* | (2006.01) |
| *G01N 1/42* | (2006.01) |
| *F16H 57/08* | (2006.01) |
| *G01N 23/20033* | (2018.01) |
| *G01N 35/02* | (2006.01) |

(Continued)

(52) U.S. Cl.
CPC ............ *G01N 1/42* (2013.01); *A01N 1/0242* (2013.01); *A01N 1/0257* (2013.01); *A01N 1/0268* (2013.01); *F16H 1/28* (2013.01); *F16H 57/08* (2013.01); *F16H 57/12* (2013.01); *F25D 3/11* (2013.01); *G01N 23/20033* (2013.01); *G01N 35/025* (2013.01); *F25B 19/005* (2013.01);

(Continued)

(58) Field of Classification Search
CPC ......... F16H 57/08; F16H 57/082; G01N 1/42; F25B 19/005
See application file for complete search history.

(56) References Cited

U.S. PATENT DOCUMENTS

| | | |
|---|---|---|
| 3,783,736 A | 1/1974 | Richardson |
| 4,034,643 A | 7/1977 | Iannucci et al. |

(Continued)

OTHER PUBLICATIONS

Planetary Indexing Systems—FIBRO GmbH; http://www.fibro.de/en/rotary-tables/product-groups/rotocutting-rotary-tables-for-machine-tools/special-solutions/planetary-indexing-systems.html; printed Feb. 5, 2018; 3 pages.

*Primary Examiner* — Mark J Beauchaine
(74) *Attorney, Agent, or Firm* — Bond, Schoeneck & King, PLLC; Frederick Price (57) ABSTRACT

A method and a cryogenic sample positioning system are provided which include: a sample holder cassette that is vertically coupled to a carousel gear through a first shaft. Each sample holder cassette has a first degree of rotation about the first shaft. A first planet drive gear underlies and is vertically coupled to the carousel gear through a second shaft that extends from the carousel gear through the first planet drive gear. The carousel gear has a second degree of rotation about the second shaft that is different from the first degree of rotation. A planet gear that is laterally connected to a second planet drive gear is interposed between each of the carousel gear and the first planet drive gear. Each of the planet gear and the second planet drive gear selectively define the first degree of rotation, without affecting the second degree of rotation of the carousel gear.

20 Claims, 5 Drawing Sheets

(51) Int. Cl.
  *F16H 57/12*  (2006.01)
  *F25D 3/11*   (2006.01)
  *A01N 1/02*   (2006.01)
  *F25B 19/00*  (2006.01)
  *G01N 35/04*  (2006.01)

(52) U.S. Cl.
  CPC ............... *G01N 2035/0486* (2013.01); *G01N 2223/604* (2013.01)

(56) References Cited

U.S. PATENT DOCUMENTS

| | | | | |
|---|---|---|---|---|
| 4,622,457 A | * | 11/1986 | Bradley | G01N 35/1079 235/375 |
| 4,849,176 A | * | 7/1989 | Sakagami | G01N 35/0095 422/64 |
| 6,158,196 A | | 12/2000 | Trebbi et al. | |
| 8,348,720 B1 | * | 1/2013 | Ko | B24B 37/042 451/285 |
| 9,193,539 B2 | | 11/2015 | Blenkinsop et al. | |

* cited by examiner

CRYOGENIC COOLING POSITIONING APPARATUS, METHODS AND APPLICATIONS

CROSS-REFERENCE TO RELATED APPLICATION

This application claims the benefit of U. S. Provisional Patent Application No. 62/365,488, filed Jul. 22, 2016, entitled "Cryogenic Cooling positioning apparatus, methods, and applications", which is hereby incorporated herein by reference in its entirety.

STATEMENT REGARDING FEDERALLY SPONSORED RESEARCH OR DEVELOPMENT

This invention was made with government support under Phase I (1R43GM101817-1) and Phase II (2R44GM101817-02) SBIR Grants awarded by the NIH and under grant MCB 1330685 awarded by the NSF. The United States Government has certain rights in the invention.

BACKGROUND

The present invention relates to the field of biotechnology. More particularly, the invention pertains to the design of systems for cooling biological samples, and to the handling and positioning of sample holders to receive and store cold samples. The invention also pertains to the more general problem of accurately positioning objects that are immersed in cryogenic fluids.

Cryogenic Sample Cooling and Handling in X-Ray Crystallography:

X-ray crystallography is the most powerful and widely used tool for determining the molecular structures of proteins, viruses, nucleic acids, and biomolecular complexes. The determination of these molecular structures is critical to modern molecular biology, and to the development of pharmaceutical treatments for various diseases and human conditions.

X-ray data collection is typically performed on crystals cooled to T=100 K or below. At room temperature, crystals of proteins, viruses and other biomolecules are rapidly damaged by X-rays. In most cases, only a fraction of the data required to determine the molecular structure can be obtained from each crystal, especially when small (10-50 μm) crystals produced in early crystallization trials are used. Growing large crystals requires careful, expensive, and time-consuming optimization. At room temperature, crystals must be handled carefully: they can easily be damaged by mechanical contact; they can dry out, causing loss of diffraction; and significant temperature changes can cause changes in protein structure. Thus, more than 98% of X-ray data is collected from crystals cooled to T~100 K. At cryogenic (e.g., T<120 K) temperatures, crystals can typically withstand X-ray doses 30-1000 times larger than at 300 K, sometimes allowing structure determination using a single crystal. Crystals are cooled by plunging them from air into liquid nitrogen or liquid propane. Cryo-cooled crystals are as hard as ice and insensitive to large temperature changes as long as the temperature remains below ~150 K, so that they can be easily stored, shipped, and manipulated at the synchrotron. Consequently, the introduction of cryocrystallographic methods for biomolecular crystallography in the 1990s was transformative.

In typical cryocrystallographic practice, a crystal is either grown in or soaked in a drop containing cryoprotectants (glycerol, ethylene glycol, 2-methyl-2,4-pentanediol (MPD), polyethylene glycol (PEG)), and harvested from the drop using a nylon or microfabricated loop attached to a metal goniometer base. It is then directly plunged by hand into an open-mouth Chamber or an open foam box filled with liquid nitrogen (in the process bringing typically ungloved fingers within centimeters of the liquid cryogen). To facilitate organization, storage, shipping, and sample management at the X-ray source, cryo-cooled samples are usually inserted into sample "carousel", "puck", or "cassette" that accepts many samples. This multiple sample holder is typically immersed in the same liquid nitrogen as is used to cool the samples, so that samples are transferred to the holder without risk of warming.

Once loaded in cryovials or multiple sample pucks, the samples are stored in cryogenic chambers or dry shippers. These are transported to an X-ray source, which may be a commercial X-ray system in the home laboratory, or a synchrotron X-ray source at a national facility. At the X-ray source, samples in pucks are loaded into a liquid-cryogen-filled container of an automated sample changer, and the automated changer then selects, pulls out of the puck, and positions each sample for X-ray examination. When X-ray measurements on a sample are complete, the automated changer returns the sample to the puck, and selects another sample for measurement. In these sample changer devices, the pucks may be stationery, and samples selected by a moving arm, or the sample holding arm may be in a fixed position, and the desired sample is translated or rotated beneath the arm.

More recently, an automated system for plunge cooling of protein crystals has been developed. In such systems, automated loading of cryogenically cooled samples into cryogenically cooled sample holding pucks/cassettes is highly desirable.

Cryogenic Sample Cooling and Handling in Cryoelectron Microscopy and in Cryopreservation of Biomolecules, Cells, and Tissues:

Aside from crystallography, many other applications involve the cryogenic cooling, storage, and subsequent retrieval of biological samples, including samples for cryoelectron microscopy, for cold storage of proteins and biologic drugs, and for cryopreservation of cells (e.g., gametes, stem cells) and tissues. In all of these applications, samples may be cooled by plunging in a liquid cryogen (liquid propane or ethane in cryoelectron microscopy, liquid nitrogen in other applications), and then transferred to a multiple sample holder that is immersed in liquid nitrogen. Multiple sample holders can then be transferred to a cryogenic temperature dry storage container. Sample cooling and transfer to the sample holder is typically done by hand, but there is increasing interest in automated systems that can improve reproducibility and reliability.

Methods for Transferring and Storing Samples Immersed in Liquid Cryogens:

Several methods are used for automated transfer of samples to, and from multiple sample holders/cassettes immersed in liquid cryogens. In one method, the multiple sample holder is held in fixed position within a liquid nitrogen containing chamber, and individual samples loaded and retrieved using a robotic arm with full x-y-z motion that accesses the samples from above the chamber. In a second method, the robotic arm is replaced by a simple vertical translation (z) arm mounted on an x-y stage, again placed above the liquid nitrogen containing chamber.

A major limitation of these approaches is that a large area of liquid nitrogen surface—at least the area of the multiple sample holder—may be exposed to ambient air, causing excessive boil-off of liquid nitrogen and accumulation of frost on cold surfaces and in the liquid nitrogen, contaminating the liquid nitrogen, and possibly also the sample. This can be addressed by using relatively complicated mechanisms such as x-y sliding chamber covers with small openings that can be translated laterally to expose each sample position, but these covers are large and bulky.

Achieving the positional accuracy required to place large numbers of samples into holders and to retrieve them is not trivial, especially if the chamber undergoes thermal cycling and/or has not reached steady state dimensions.

A potentially simpler approach that can minimize exposure of the liquid nitrogen to ambient air, minimize boil-off, and minimize accumulation of ice is to translate samples only along a single axis (rather than in x, y and z axes), that passes through a small fixed opening in a lid that covers and insulates the liquid nitrogen chamber. Samples can be translated along this axis into the liquid nitrogen for cooling, and then translated along this axis within the liquid nitrogen and inserted into a sample holder.

This approach requires a mechanism that operates in liquid nitrogen for holding samples in one or more cassettes, each with multiple sample positions, and for positioning one or multiple cassettes each with multiple sample positions so as to place a particular sample position in a particular sample cassette directly along the sample translation axis, so that samples can be loaded and retrieved with a simple single axis linear motion. Sample holder cassettes could then be removed, cryogenically stored, shipped to another location, and transferred into a liquid nitrogen chamber with a similar sample holder cassette positioner, vertical (or tilted) sample translation axis, and a small access hole in a chamber cover, from which samples could be retrieved.

SUMMARY

In view of the above discussion, the inventors recognized that the sample holder cassette positioning mechanism should be as compact as possible, to reduce the volume of liquid nitrogen required to initially cool samples and sample holder cassettes, and to maintain the mechanism and sample holder cassettes at cryogenic temperatures as compared to conventional systems. Various embodiments of the present invention may be advantageous in that they may solve or reduce one or more of the potential problems and/or disadvantages discussed herein.

The present invention relates, inter alia, to the design, function and use of cryogenic cooling systems for accurately positioning samples and one or more sample holder cassettes. More specifically, it relates to positioning of cryogenically cooled samples and sample holder cassettes, including those that are immersed in liquid cryogens like liquid nitrogen. The particular focus is on sample holder cassettes in X-ray cryocrystallography, but the invention can be used in any sample positioning application, especially those in which samples are immersed in cryogenic liquids.

Further, the present application describes a sample positioning system for use in X-ray cryocrystallography and in cryogenic sample coolers. The objectives in designing and implementing this system were that it accepts several sample holder "cassettes", each sample holder cassette be capable of holding multiple samples (e.g., as used in cryocrystallography), that it be able to accurately position any sample location in any cassette at a precise location; and that it be able to reliably do so during operation in liquid nitrogen for periods of about 48 hours to about one week.

In one aspect of the present application, a cryogenic sample positioning system is provided. The cryogenic sample positioning system includes: at least one sample holder cassette comprising at least one opening, that is vertically coupled to an upper surface of a carousel gear through a first axle shaft, wherein the at least one sample holder cassette has a first degree of rotation about the first axle shaft; a first planet drive gear underlying and vertically coupled to the carousel gear through a second axle shaft that extends from the carousel gear through the first planet drive gear, wherein the carousel gear and the at least one sample holder cassette each have a second degree of rotation about the second axle shaft that is independent of the first degree of rotation; and at least one planet gear that is laterally connected to a second planet drive gear, and is interposed between each of the carousel gear and the first planet drive gear, wherein each of the at least one planet gear and the second planet drive gear selectively define the first degree of rotation, without affecting the second degree of rotation of the carousel gear.

According to an embodiment, the at least one planet gear is vertically coupled to the at least one sample holder cassette through the first axle shaft, wherein the at least one planet gear is isolated from the underlying first planet drive gear.

According to an embodiment, the first and the second planet drive gears are rigidly connected to each other, and are connected to the carousel gear through the second axle shaft, the first and the second planet drive gear being co-axially rotatable about the second axle shaft independent of the rotation of the carousel gear.

According to an embodiment, the at least one planet gear is rotatable by the first planet drive gear through the second planet drive gear, wherein the rotation of each of the first planet drive gear, the at least one planet gear and the second planet drive gear facilitates defining the rotation of the at least one sample holder cassette about the first axle shaft.

According to an embodiment, the cryogenic sample positioning system further comprises a bushing adjoining the second axle shaft, wherein the bushing laterally separates the carousel gear, and the first and the second planet drive gears from the second axle shaft, the bushing comprising a material that has a thermal coefficient of expansion substantially equal to that of stainless steel.

According to an embodiment, the cryogenic sample positioning system further comprises a first pinion gear laterally coupled to the first planet drive gear, and a second pinion gear laterally coupled to the carousel gear, wherein each of the first pinion gear and the second pinion gear are configured to discretely rotate each of the carousel gear and the first planet drive gear.

According to an embodiment, the cryogenic sample positioning system further comprises a first pinion shaft that is attached to the first pinion gear, wherein rotation of the first pinion shaft and the first pinion gear define rotation of the at least one planet gear and the corresponding sample holder cassette of the at least one sample holder cassette about the first axle shaft.

According to an embodiment, the cryogenic sample positioning system further comprises a second pinion shaft that is attached to the second pinion gear, wherein rotation of the second pinion shaft and the second pinion gear define rotation of the carousel gear that is independent of the rotation of the underlying first and the second planet drive gears.

According to an embodiment, the at least one planet gear has a diameter that is less than a diameter of the carousel gear.

According to an embodiment, the cryogenic sample positioning system is enclosed in a cryogenic chamber having an opening, wherein the at least one opening of the at least one sample holder cassette is directly aligned with the opening of the cryogenic chamber so as to accurately position a sample within the at least one opening.

In another aspect of the present invention, a method is provided that includes: providing a cryogenic sample positioning structure, comprising: at least one sample holder cassette comprising at least one opening is vertically coupled to an upper surface of a carousel gear through a first axle shaft, wherein the at least one sample holder cassette has a first degree of rotation about the first axle shaft; a first planet drive gear underlying and vertically coupled to the carousel gear through a second axle shaft that extends from the carousel gear through the first planet drive gear, wherein the carousel gear and the at least one sample holder cassette each have a second degree of rotation about the second axle shaft that is independent of the first degree of rotation; and at least one planet gear that is laterally connected to a second planet drive gear, and is interposed between each of the carousel gear and the first planet drive gear, wherein each of the at least one planet gear and the second planet drive gear selectively define the first degree of rotation, without affecting the second degree of rotation of the carousel gear; and disposing the cryogenic sample positioning structure within a cryogenic chamber having an opening, wherein the at least one opening of the at least one sample holder cassette is directly aligned with the opening of the cryogenic chamber so as to accurately position a sample within the at least one opening.

According to an embodiment, the step of providing comprises providing the at least one planet gear that is vertically coupled to the at least one sample holder cassette through the first axle shaft, wherein the at least one planet gear is isolated from the first planet drive gear.

According to an embodiment, the first and the second planet drive gears are rigidly connected to each other, and are connected to the carousel gear through the second axle shaft, the first and the second planet drive gear being co-axially rotatable about the second axle shaft independent of the rotation of the carousel gear.

According to an embodiment, the at least one planet gear is rotatable by the first planet drive gear through the second planet drive gear, wherein the rotation of each of the first planet drive gear, the at least one planet gear, and the second planet drive gear facilitates defining the rotation of the at least one sample holder cassette about the first axle shaft.

According to an embodiment, the method further comprises providing a first pinion gear that is laterally coupled to the first planet drive gear, and a second pinion gear that is laterally coupled to the carousel gear, wherein each of the first pinion gear and the second pinion gear are configured to discretely rotate each of the carousel gear and the first planet drive gear.

According to an embodiment, the method further comprises providing a first pinion shaft that is attached to the first pinion gear, wherein rotation of the first pinion shaft and the first pinion gear define rotation of the at least one planet gear and the corresponding sample holder cassette of the at least one sample holder cassette about the first axle shaft.

According to an embodiment, the method further comprises providing a second pinion shaft that is attached to the second pinion gear, wherein rotation of the second pinion shaft and the second pinion gear define rotation of the carousel gear that is independent of the rotation of the underlying first and the second planet drive gears.

According to an embodiment, the method further comprises providing a bushing adjoining the second axle shaft, wherein the bushing laterally separates the carousel gear, and the first and the second planet drive gears from the second axle shaft, the bushing comprising a material that a thermal expansion of coefficient equal to that of stainless steel.

According to an embodiment, the at least one planet gear has a diameter that is less than a diameter of the carousel gear.

According to an embodiment, the method further comprises providing a fiber-optic sensor within the cryogenic chamber, the fiber-optic sensor facilitating determining positioning of the at least one sample holder cassette relative to that of the opening of the cryogenic chamber.

Additionally, in one embodiment, the rotation of the carousel gear and the at least one sample holder cassette are independent of the rotation of the underlying first planet drive gear. Further, the at least one planet gear is isolated from the underlying first planet drive gear in the direction of the first axle shaft. In another embodiment, the bushing that laterally separates the first and the second planet drive gears from the second axle shaft also vertically separates the carousel gear from the second planet drive gear. In another embodiment, each sample holder cassette is vertically coupled to a sample holder platform rather than to the first axle shaft, and the sample holder platform is vertically coupled to an upper surface of a carousel gear through a first axle shaft. Still further, in an embodiment, the cryogenic sample positioning structure is enclosed in a cryogenic chamber filled with a cryogenic liquid to a level such that the sample holder cassettes are fully immersed, wherein the chamber has an opening in a top surface, wherein at one time any opening in the at least one sample holder cassette is directly aligned with the opening in the top surface of the cryogenic chamber so as to accurately position the opening of the at least one sample holder cassette on an axis passing through the opening, and where a sample is translated along this axis between ambient and the opening of the at least one holder cassette, and undergoes cryogenic cooling as it passes from the surface of the liquid cryogen to the opening of the at least one sample holder cassette.

Additional features and advantages are realized through the techniques of the present invention. Other embodiments and aspects of the invention are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific example, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

The present invention relates to, inter alia, a method and a cryogenic sample positioning system for precise positioning of samples, and in particular, samples cooled by and immersed in liquid cryogens. By way of example, the cryogenic sample positioning system disclosed herein comprises an epicyclic continuously indexing mechanism with a planet drive gear (commonly referred to as "sun gear"), a carousel gear (commonly referred to as a "planet gear carrier") and one or more planet gears driven from the edges by extending the planet drive gear out to a large diameter.

Figure 1:
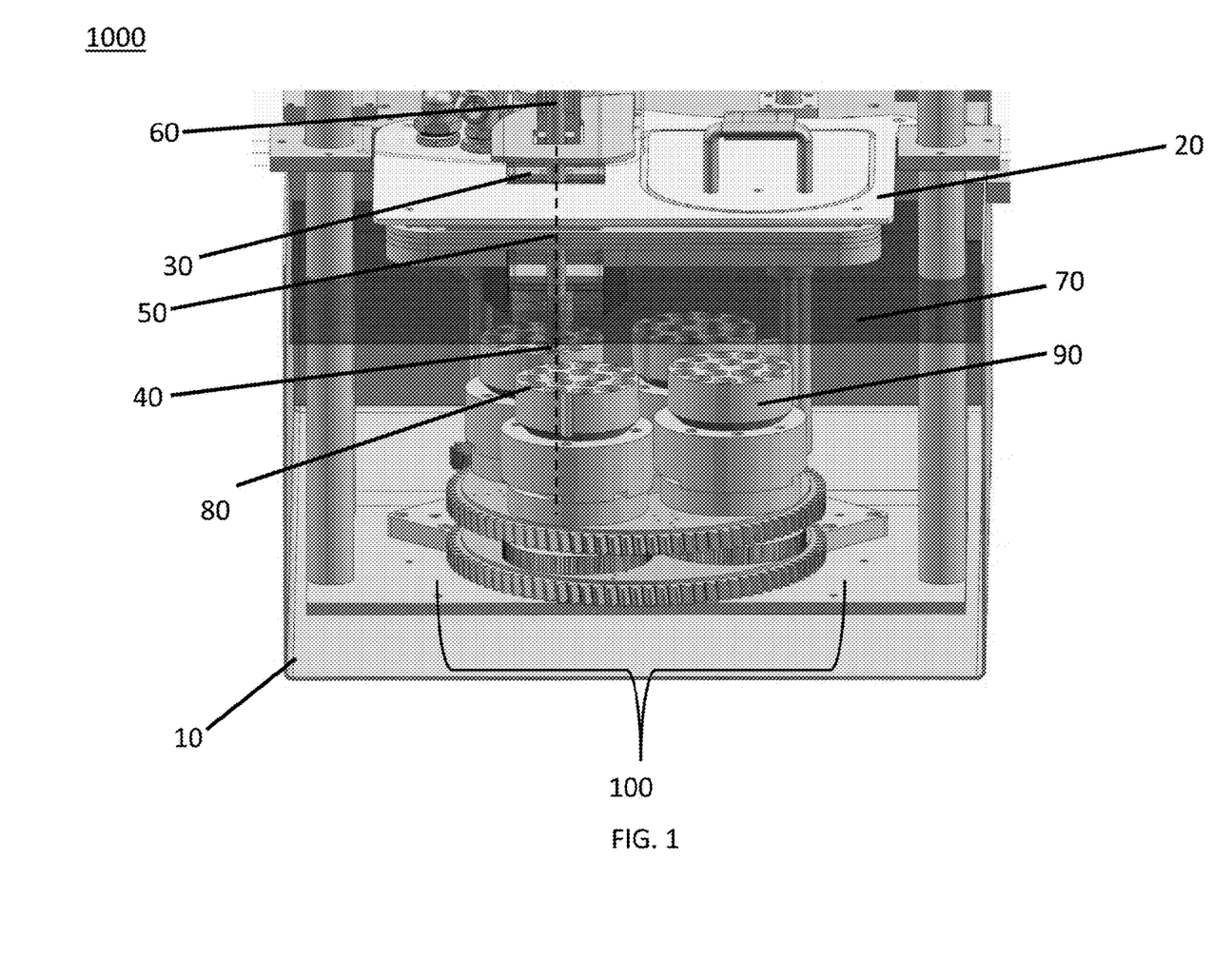
FIG. 1 illustrates a section view of one embodiment of a cryogenic cooling and storage system for use, for instance, with accurate positioning and storage of samples in a cryogenic liquid, in accordance with one or more aspects of the present invention.

FIG. 1 depicts a cross-sectional view of an exemplary cryogenic cooling and storage system 1000 that includes: a thermally insulated liquid nitrogen filled chamber 10, a cover or lid 20 for the chamber having a passage 30 through which a sample 40 may be positioned in a cryogenic sample positioning system 100. The sample 40 can be translated along a single axis 50 by the vertical translation stage 60 into the liquid nitrogen 70 for cooling and then into one of several openings 80 (also referred disclosed herein as "sample holder receptacles") in one of several sample holder cassettes 90 of the cryogenic sample positioning system 100. In one embodiment, the cryogenic sample positioning system 1000 disclosed herein positions a desired opening 80 in a desired sample holder cassette 90 directly along the vertical axis 50 of the translation stage 60, allowing the sample 40 to be inserted into or removed from that position in the sample holder cassette. As described further below in greater detail, and in one embodiment, positioning of a sample holder cassette involves rotating the sample holder cassette about its central axis of the sample positioning system (for instance, analogous to orbital motion of a planet about the sun), and rotating the sample holder cassette about its planetary axis. The combination of these two motions allows any sample receptacle position on any sample holder to be positioned along the axis of the sample translation stage.

Figure 2A:
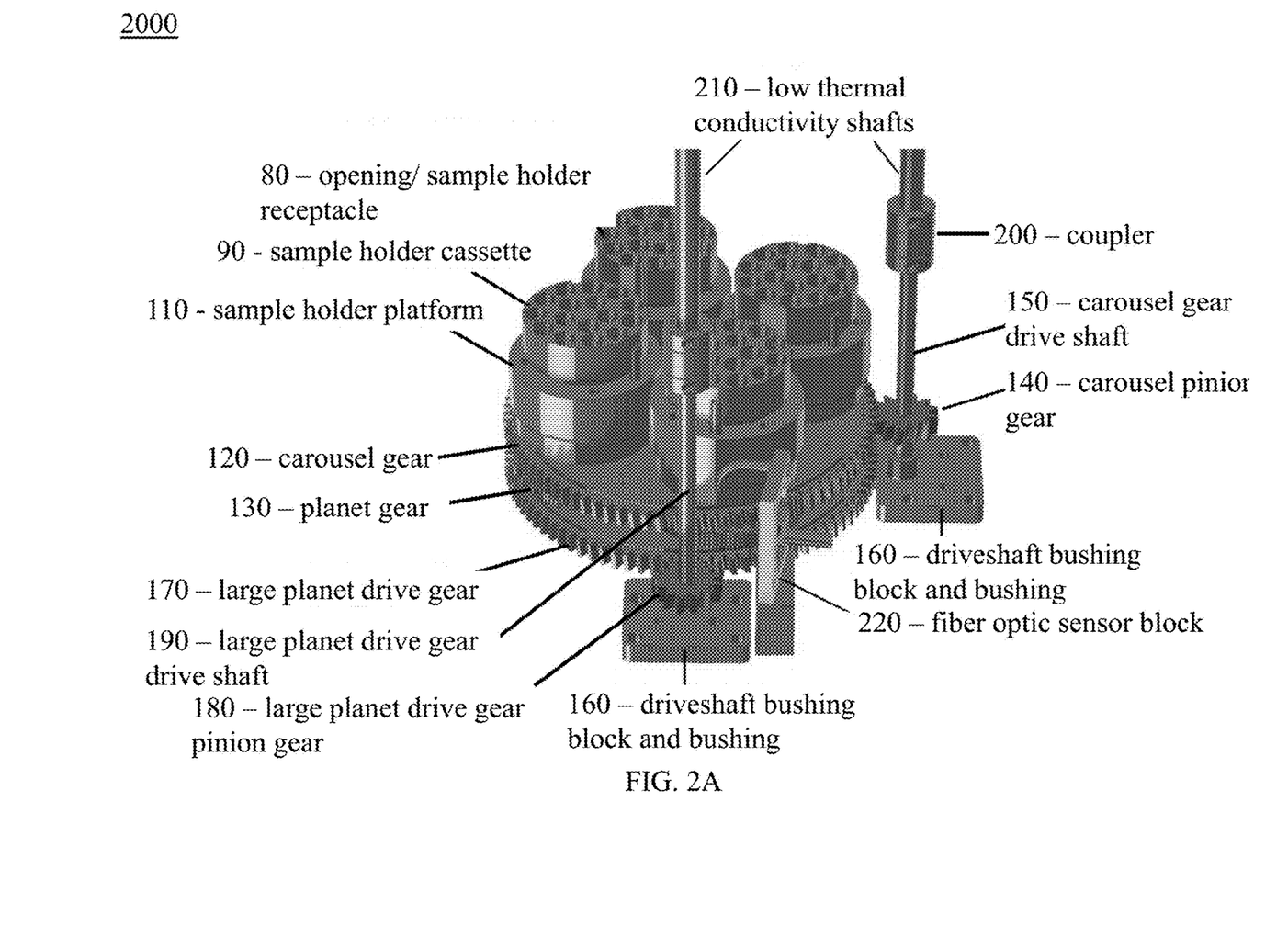
FIG. 2A depicts a cross-sectional view of the cryogenic cooling system, in accordance with one or more aspects of the present invention.

FIG. 2A shows a cross-sectional view of the cryogenic sample positioning system 2000, in accordance with one or more aspects of the present invention. As depicted, the cryogenic sample positioning system 2000 includes one or more removable sample holder cassette(s) 90 (commonly referred to as "pucks" in the nomenclature of X-ray crystallography), that rest on and are vertically coupled to an upper surface of a corresponding sample holder platform 110. In one embodiment, each sample holder cassette(s) 90 includes one or more openings 80 (also referred to herein as "sample holder receptacles"), and can be used to position samples that can be immersed in a cryogenic liquid. Further, although the depicted sample holder cassette(s) 90 are circular, one skilled in the art will understand that each of the sample holder cassette(s) 90 as well as the openings 80 disposed therein can be of any shape and dimension. As understood, each of the sample holder cassette(s) 90, as well as the corresponding sample holder platform 110 are further vertically coupled to an upper surface of a carousel gear 120 through the planet gear axle shaft 230 (see FIG. 2B).

Figure 2B:
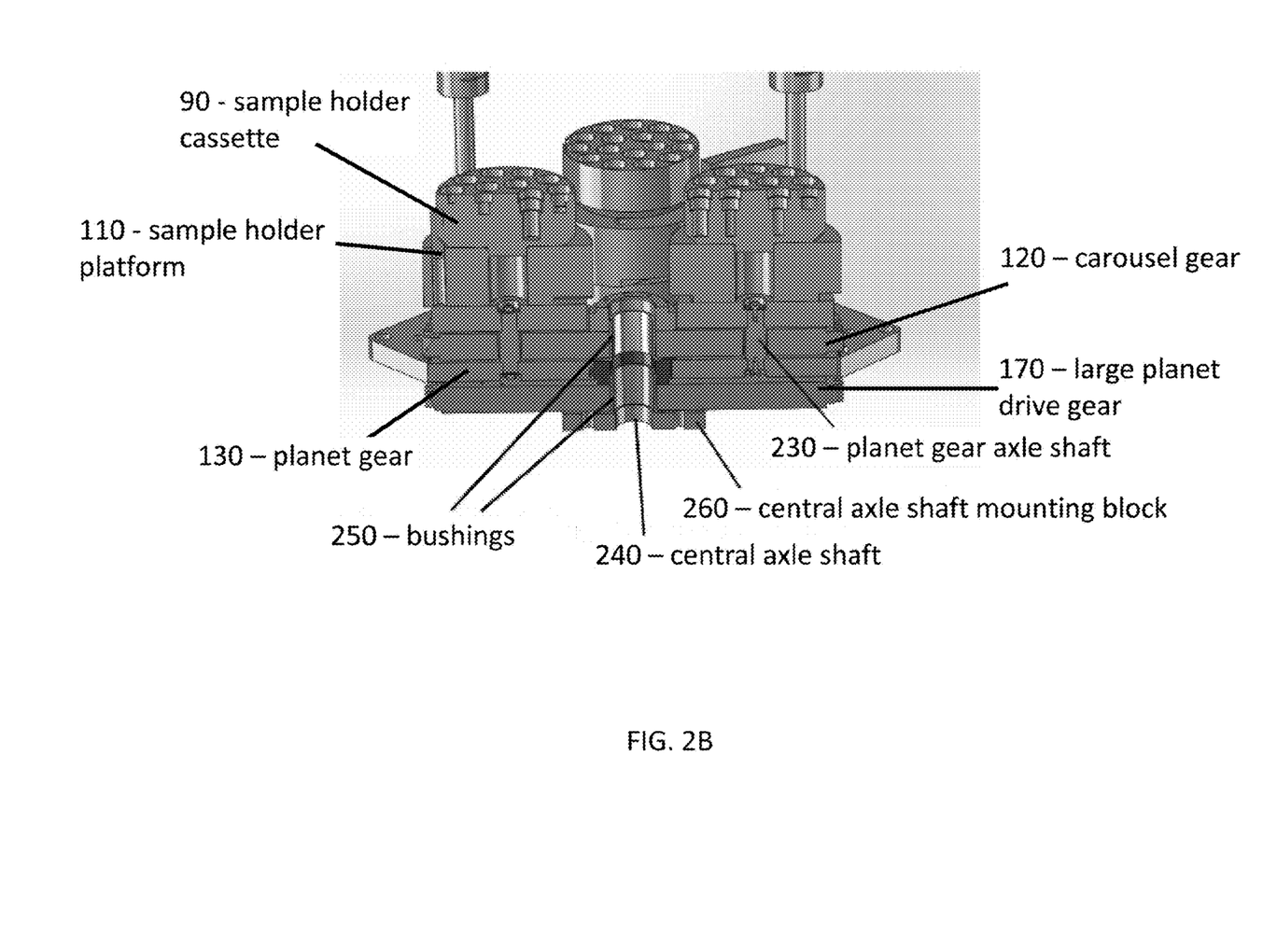
FIG. 2B depicts a cross-sectional view of the cryogenic cooling system, in accordance with one or more aspects of the present invention.

Further, the planet gear axle shaft 230 (see FIG. 2B) passes through the carousel gear 120 and is attached to a corresponding planet gear 130 disposed below a lower surface of the carousel gear 120. In one embodiment, each of the planet gear(s) 130 are laterally connected to a small planet drive gear 270 (see FIG. 2D) (which, for instance, can be commonly referred to as a "sun gear"). Although the ratio of the planet gear(s) 130 to the small planet drive gear 270 can be any ratio within the physical design constraints, in one example, the ratio of the planet gear 130 to the small planet drive gear 270 may be about 2:1. In another embodiment, although FIG. 2B depicts that the diameter of the planet gear(s) 130 is larger than that of the carousel gear 120 for the sake of clarity, the diameter of each of the planet gear(s) 130 is actually less than a diameter of the carousel gear 120, while the diameter of the planet gear(s) 130 may be greater than that of small planet drive gear 270. According to an embodiment, the carousel gear 120 is laterally connected to and discretely rotated by the carousel pinion gear 140 and carousel gear drive shaft 150, without affecting an underlying large planet drive gear 170. Each of the sample holder cassette(s) 90, corresponding sample holder platforms 110, and the corresponding planet gear(s) 130 are fixed to their own common shaft (i.e., shaft 230 (FIG. 2B)) and rotate together, thereby providing a first degree of rotation to the sample holder cassette 90 about the planet gear axle shaft 230 (see FIG. 2B). Further, when the carousel gear 120 is rotated, each of the planet gear(s) 130, sample holder platforms 110, and sample holder cassette(s) 90, all rotate about the central axis of the carousel gear 120 (which for instance, is similar to an orbital motion of planets about the sun), thereby providing a second degree of rotation that is independent of the first degree of rotation.

Although not critical to the invention, and as one skilled in the art will understand, the planet gear axle shaft 230 (see FIG. 2B) is formed within a bore, and is separated from the carousel gear 120, for instance, via a bushing (not shown). These bushings (not shown) are press-fit into the carousel gear 120, and are machined to size after press-fitting. In such example, the annular section portion of the bushing faces upwards, and accepts the vertical load (weight) of the sample holder platform 110 and sample holder cassette(s) 90 attached to the planet gear axle shaft 230 (see FIG. 2B) passing through that bushing. In one example, the size of the bushing (not shown) has been defined by the size of the bore, and the bushing may be formed of, or may include, a material that has a coefficient of thermal expansion that is substantially equal to a coefficient of thermal expansion for stainless steel (which, for instance, is lower than that of aluminum). In one example, the bushing (not shown) may be formed, or may include a material such as, impregnated polyether ether ketone (PEEK) material. Further, in another embodiment, the bushings 250 (FIG. 2B) in the central axle shaft 240 of the carousel gear 120 supports the weight of the carousel gear 120, the sample holder cassette(s) 90, sample holder platform(s) 110, and the multiple planet gear(s) 130 by transferring the load to an underlying large planet drive gear 170. This load, in turn, is transferred to the central axle shaft mounting block 260 (see FIG. 2B), as described further below in greater detail.

Continuing with FIG. 2A, the sample holder cassette(s) 90, carousel gear 120, and planet gear(s) 130 are vertically coupled to the large planet drive gear 170 through an axle placed in the central axle shaft 240 (see FIG. 2B). Although not critical to the invention, in one example, the size of the carousel gear 120 may be equal to the size of the large planet drive gear 170, while in another example, the size of the carousel gear 120 may be different to the size of the large planet drive gear 170. Although not critical to the invention, and as one skilled in the art will understand, the central axle shaft 240 (see FIG. 2B) is formed within a bore (see FIG. 2B), and is separated from the small planet drive gear 270, for instance, via a bushing 250 (see FIG. 2B). For instance, the bore (see FIG. 2B) has been defined by a bushing and is formed of a material that has a coefficient of thermal expansion that is substantially equal to a coefficient of thermal expansion for stainless steel (which, for instance, is lower than that of aluminum). In one example, the bushing may be formed, or may include a material such as, impregnated polyether ether ketone (PEEK) material. As one skilled in the art will understand, impregnated PEEK bushing 250 (which, for instance, is a proprietary formula product from Igus® inc.) has been found to give excellent performance for all of the in-liquid nitrogen (LN2) bushings. This material that, for instance, has conventionally been designed for high temperature use, has been utilized in the present invention for a cryogenic use. As understood, this material resists wear and cracking. Advantageously, the coefficient of thermal expansion (that, for instance, is substantially equal to that of stainless steel) of the bushings utilized in the present invention, facilitates avoiding various loose connections and bushing seizing. In one embodiment, the bushing 250 (FIG. 2B) has been affixed to the small planet drive gear 270 and the large planet drive gear 170 by conventional press fits, and is machined to final size after conventional press fitting processes. Further, the bushing 250 of the large planet drive gear 170 has an annular section (see FIG. 2B) below the large planet drive gear 170 which, for instance, may be used to support the vertical thrust load (weight) of the large planet drive gear 170, and the other rotating components of the carousel gear 120. As understood, the top portion of this annular section of the bushing 250 rotates with the large planet drive gear 170, while the bottom portion of the bushing 250 rotates against a stainless steel central axle shaft mounting block 260, as depicted in FIG. 2B.

Note that, in one embodiment, each of the planet gear(s) 130 is isolated from the underlying large planet drive gear 170, and thus, is configured to be rotatable only with the small planet drive gear 270, for instance, via the central axle shaft 2400 (see FIG. 2B). For instance, the rotation of the large planet drive gear 170 facilitates rotation of the small planet drive gear 270 which, in turn, rotates the planet gear(s) 130. This, for instance, facilitates defining the rotation of the sample holder cassette(s) 90, sample holder platform 110 and the corresponding planet gear 130 together about the planet gear axle shaft 230 (see FIG. 2B), thereby providing the first degree of rotation about the planet gear axle shaft 230 (see FIG. 2B). Further, when the carousel gear 120 is rotated, each of the planet gears 130, sample holder platforms 110, and sample holder cassette(s) 90, all rotate about the axis of the carousel gear 120 (which, for instance, is similar to an orbital motion of planets about the sun), thereby providing a second degree of rotation to the sample holder cassette 90 about the central axle shaft 240 (see FIG. 2B) as described further below in greater detail. Additionally, the large planet drive gear 170 is laterally connected to and discretely driven by the pinion gear 180 and the large planet drive gear drive shaft 190. For instance, the rotation of pinion gear 180 and the large planet drive gear drive shaft 190 define rotation of the planet gear(s) 130 and, in turn, the corresponding sample holder cassette 90 about the planet gear axle shaft 230 (see FIG. 2B). Further, note that in one embodiment, the ratio of sizes between the pinion and the corresponding gears (i.e., either pinion gear 140 to carousel gear 120 or pinion gear 180 to the large planet drive gear 170) may not be significant for optimal performance, although one skilled in the art will understand that the larger gear ratios provide increased accuracy. Additionally, the exact form of the gear teeth can be critical in certain embodiments for minimizing backlash. As one skilled in the art will understand that the backlash refers to the gap between two meshing gears, and that the more the number of smaller teeth of a gear disclosed herein, the less will be the backlash.

Still further, in one embodiment, each of the carousel gear drive shaft 150 and the large planet drive gear drive shaft 190 are positioned on the same side of the assembly, and extend out of the liquid cryogen to the ambient temperature environment, and thus, eliminating the need for expensive cryogenic drive motors. At their lower end, these shafts are connected to, and are held in place by driveshaft bushing blocks and the corresponding bushings 160. Additionally, although not critical to the invention, each of these drive shafts (i.e., carousel gear drive shaft 150 and large planet drive gear drive shaft 190) are connected, for instance, via couplers 200, to low thermal conductivity shafts 210 that, in turn, are connected to two discrete motors (not shown). In one example, the low thermal conductivity shafts 210 may be formed of, or may include a material such as, for instance, G10 fiberglass which for instance, can bridge the temperature transition (i.e., from ambient temperature to −196° C. gas and then into the liquid nitrogen). As understood, each of these motors can be operated at an ambient temperature. The low thermal conductivity shafts 210 can, for instance, reduce heat transfer from the motors through each of the shafts (i.e., carousel gear drive shaft 150 and large planet drive gear drive shaft 190) and into the liquid nitrogen, thereby reducing consumption of the liquid nitrogen within the cryogenic chamber (FIG. 1), and also minimize accumulation of frost on the portions of the shafts that are exposed to ambient air. Note that, in one embodiment, each of the pinion shafts (i.e., carousel gear drive shaft 150 and large planet drive gear drive shaft 190), for instance, may include, or may be fabricated of stainless steel, and onto which the pinion gears (i.e., carousel pinion gear 140 and large planet drive gear pinion gear 180) are press fit.

Still further, although not critical to the invention, the pinion gears shafts use a smaller version of the same type of impregnated-PEEK bushing (not shown) as each of the carousel gear 120 and the large planet drive gear 170. Each bushing (not shown) is press-fit into its respective pinion shaft support block (not shown) with the annular thrust face facing upwards, and has been machined to size after the press-fitting process. In one example, the annular thrust bearing face of the large planet drive gear pinion shaft bushing (not shown) supports the weight of the pinion shaft via the lower face of the large planet drive gear pinion gear 180. In another example, the annular thrust bearing face of the carousel gear pinion shaft bushing (not shown) supports the weight of the pinion shaft 150 via a machined detail in the shaft.

Additionally, although not critical to the invention, Teflon seals (not shown) are disposed between the top lid or cover of the liquid nitrogen filled chamber and the low thermal conductivity shafts 210 that protrude through the top lid or the cover thereof, allow driving the shafts while preventing cold gas leakage toward the ambient environment, and moist air from the ambient environment from entering the enclosed cryogenic chamber and causing accumulation of the ice. Advantageously, while the Teflon seals prevent leakage of the gas from the cryogenic chamber and the low thermal conductivity of the G10 fiberglass shaft material reduces heat transfer from ambient temperature to the liquid cryogen bath and the cryogenic bath boil-off. Additionally, low thermal conductivity of the shaft material 210 also ensures that the projection of the shaft into the ambient temperature remains at a temperature above the dew point. This, for instance, prevents all icing at and near pinion shafts, without heat applied beyond the heat applied to the underside of the lid of the cryogenic chamber container. The excellent dimensional stability of G10 fiberglass material also ensures that seals with the shaft remain tight.

Figure 2C:
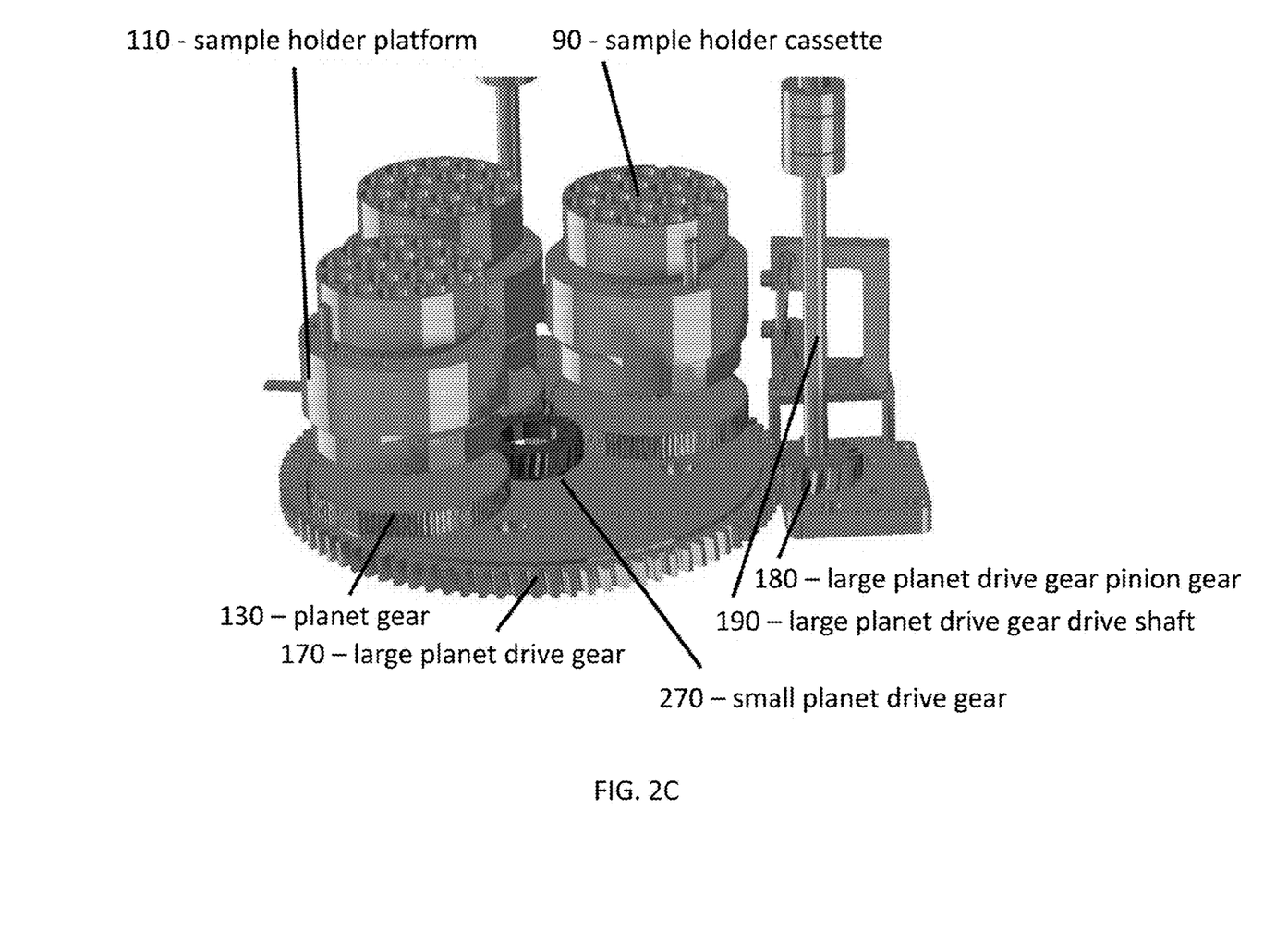
FIG. 2C depicts a cross-sectional view of the cryogenic cooling system, in accordance with one or more aspects of the present invention.
Figure 2D:
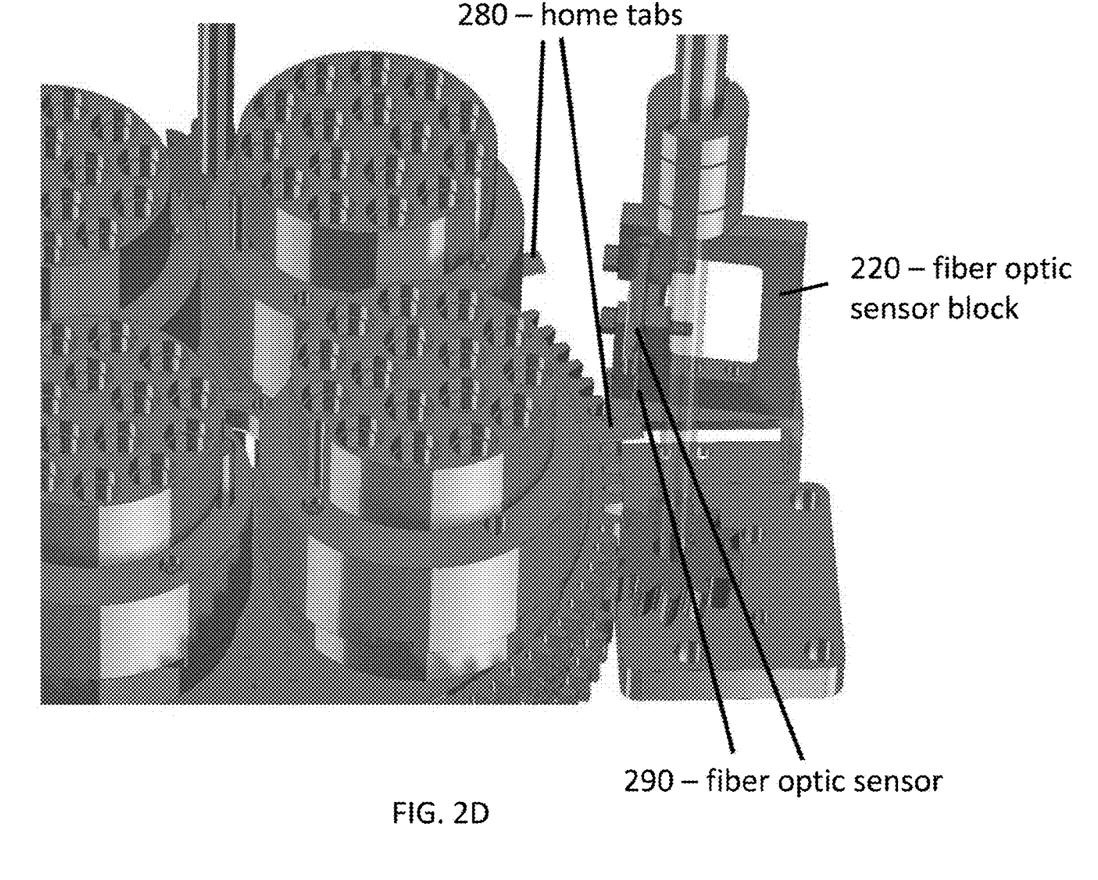
FIG. 2D depicts a cross-sectional view of the cryogenic cooling system, in accordance with one or more aspects of the present invention.

Still further, a fiber optic-based sensing system 290 that is capable of performing measurements in liquid nitrogen is coupled to the carousel gear 120, as depicted in FIG. 2D. Such a fiber optic-based sensor held in place by the sensor block 220 facilitates determining the position of the carousel gear 120 and the planet drive gears 130 and 270, and thus the position of the sample holder platforms and cassettes. Further, the carousel gear 120 and one of the sample holder platforms 110 have tabs 280 which are sensed using a remote light-beam sensor via fiber optic elements 290 that extend into and remain beneath the liquid nitrogen. The system also includes an assembly for sensing the liquid cryogen level, to ensure that samples are always immersed in liquid cryogen and do not warm up.

According to an embodiment the rotational position of the first planet drive gear and carousel gear are known at all times by tracking the rotation of the first and second pinion shafts after registering at startup of the device the precise positions of the first planet drive gear and carousel gear. The position of the carousel gear is registered at startup by rotating the carousel gear until a steel tab attached to the carousel gear blocks the light beam of a fiber optic sensor immersed in liquid cryogen. The blocking of the light beam indicates the carousel gear is in a precise known rotational position. The position of the first planet drive gear is registered at startup by a steel tab attached to one of the at least one attachment points for the at least one sample holder cassette blocking the light beam of the fiber optic sensor. The blocking of the light beam indicates the sample holder cassette is in a precise known position. The carousel gear position is determined first and then this positioning knowledge is used to position the at least one sample holder cassette attachment point with the steel tab at the fiber optic sensor.

When a sample position is indexed, the approach is always from the same rotational direction ('forwards') such that the calibrated positions are not offset due to the gear train backlash (backlash compensation), negating the need for mechanical backlash adjustment at assembly or mechanical backlash compensation. To avoid a 'long way around' trip that might result from enforcing this directional rule, a position can be reached by rotating the gears in the 'backwards' direction but overshooting the position, then approaching the desired position in the 'forwards' direction Further, in one embodiment, the rotational motion of the sample holder platform(s) 110, sample holder cassette(s) 90, and planet gear(s) 130 about their planetary axis has been described in greater detail in connection with FIG. 2C. Note that, as depicted in FIG. 2C, in one embodiment, the carousel gear 120 has been removed for ease of understanding. Rotation of the planet gear(s) 130 about their axis is driven by the small planet drive gear 270, which is rigidly attached (i.e., bolted) to the large planet drive gear 170, so that these two gears form a compound gear. The planet gear(s) 130 are not fixed to the surface of the large planet drive gear 170, but are free to undergo rotational and orbital motion above it. As described above, motion of the large planet drive gear 170 is driven by the pinion gear 180 attached to the large planet drive gear drive shaft 190. Rotation of the large planet drive gear drive shaft 190 and pinion gear 180 cause rotation of the large planet drive gear 170 in the opposite sense. Rotation of the large planet drive gear 170 causes rotation of the small planet drive gear 270, which causes rotation of all of the planet gear(s) 130, sample holder platforms 110, and sample holder cassette(s) 90 in the opposite direction, and in the same direction as the pinion gear 180 of the large planet drive gear 170, thereby providing the large planet drive gear 170 with a second degree of rotation that is independent of the first degree of rotation.

Further, in an additional embodiment, the "orbital" position of the planet gear(s) 130 and sample holder cassette(s) 90 has been fixed by the carousel gear 120 (see FIG. 2A). By way of example, in one embodiment, when the carousel gear drive shaft 150 and the carousel pinion gear 140 are rotated, while the large planet drive gear drive shaft 190 is held fixed, the carousel gear 120 rotates in a direction opposite to the pinion gear 140, and the sample holder cassette(s) 90 undergo orbital motion about the center of the carousel gear 120 (i.e., via the central axle shaft 240 (see FIG. 2B)). At the same time, the planet gear(s) 130 are forced to rotate by their connection to the (in this case) stationary small planet drive gear 270, so the sample holder cassette(s) 90 also rotate about their axes. In order for the sample holder cassette(s) 90 to undergo pure orbital motion without rotation, both drive shafts (i.e., carousel gear drive shaft 150 and large planet drive gear drive shaft 190) and pinion gears (i.e., pinion gear 140 & pinion gear 180) should rotate together.

All gears associated with sample holder cassette(s) 90 (i.e., planet gear(s) 130) are driven by the same small planet drive gear 270 and large planet drive gear 170, and thus all rotate about the axes of planet gear 130 at the same time. The combination of rotation of the planet gears 130 and rotation of the carousel gear 120 provides two degrees of freedom that allows the positioning of any sample in any of the sample holders at any location within an annulus of inner and outer radii determined by the radial distance of each sample from the center of the sample holder and by radial distance of the sample holder gear axis from the central axis of the carousel gear.

When both pinion gears are rotated in the same direction at the same speed, the position of the centers of the sample holder cassette(s) 90 (and therefore the cassettes themselves) is translated around the central shaft without their orientation to the large planet drive gear or carousel gear being altered. When the large planet drive gear pinion gear is rotated with the carousel gear pinion gear held in place the sample holder cassette(s) 90 rotate in place, the location of the centers of their axles not changing.

Example Implementation:

Some example parameters of prototype sample handling systems, in accordance with one or more aspects of the present invention. Codes refer to CAD drawings.

Carousel gear train:
Carousel pinion drive gear 140: (G6.000.00/G5.900.00)
Number of Teeth: 15, Pitch Diameter: 30.225 mm, Normal Module, 2.000 mm, Pressure angle: 20°, Helical angle: 7°.
Carousel gear 120: (G5.000.00/G4.900.00)
Number of Teeth: 102, Pitch Diameter: 205.532 mm, Normal Module, 2.000 mm, Pressure angle: 20°, Helical angle: 7°
Carousel gear train gear ratio: 6.8 (i.e., carousel pinion rotates 6.8 times, carousel gear rotates once.)
Sample holder/planet gear train:
pinion drive gear 180: (G6.000.00/G5.900.00)
Number of Teeth: 15, Pitch Diameter: 30.225 mm, Normal Module, 2.000 mm, Pressure angle: 20°, Helical angle: 7°
Large planet drive gear 170: (G5.000.00/G4.900.00)
Number of Teeth: 102, Pitch Diameter: 205.532 mm, Normal Module, 2.000 mm, Pressure angle: 20°, Helical angle: 7°
Small planet drive gear 270; (G3.000.00/G2.900.00)
Number of Teeth: 40, Pitch Diameter: 40.309 mm, Normal Module, 1.000 mm, Pressure angle: 20°, Helical angle: 7°
Planet gear 130 (G2.000.00/G1.900.00)
Number of Teeth: 80, Pitch Diameter: 80.594 mm, Normal Module, 1.000 mm, Pressure angle: 20°, Helical angle: 7°
Gear Ratio: 13.6 (i.e., large planet drive gear pinion gear rotates 13.6 times, planet gear (and sample cassette holder) rotate once)

According to an embodiment, in the above example implementation, "Teeth" is a count of the number of teeth on the gear, each 'tooth' being the projection from the edge of the gear. One skilled in the art will understand that the number of teeth by itself does not specify the size of the gear. A gear size is determined by its diameter, and it has a certain number of teeth, the spacing of the teeth being the pitch (teeth per inch in one example). For a given pitch and number of teeth there is only one possible diameter. Pitch diameter is the diameter of the gear at specific calculated point on the gear teeth. Helical angle is the measure of how much the gear tooth is tilted away from a line directly through the gear.

Several variations on the embodiments described here are possible. The second planet drive gear, rather than being a small diameter gear 270 affixed to the first planet drive gear 170 as in FIG. 2(C), can be an inward-pointing geared surface running on an internal circumference of the first planet drive gear, as in the ring gear of a standard planetary gear set.

The sample holder platforms can have machined geared surfaces around the bottom circumference, with no axle supporting them and no separate planet gear, so that the sample holder platforms act as floating planet gears. Their bottom surface can include sliding bushings.

The small planet drive gear 270 can have a larger or smaller diameter than the at least one planet drive gears. The large planet drive gear 170 can have a diameter equal to, larger than, or smaller than the carousel gear 120, with appropriate changes in the diameter and/or radial position of the large planet drive gear pinion gear 180.

A single drive shaft or two coaxial drive shafts coming from above the carousel and large planet gears can be used to drive these gears from the center rather than their outer edges. For example, the carousel gear rotates on a rotating central axle, the sun gear is attached to that central axle, the central axle is driven from above.

The carousel and/or large planet gears can be driven by right-angle gear drive shaft coming in from the side, with a right-angle gearbox replacing the pinion gear.

The stacking of the gears can be altered. For example, the small and large planet drive gears can be placed above the carousel gear.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A cryogenic sample positioning system, comprising:
at least one sample holder cassette comprising at least one opening, that is vertically coupled to an upper surface of a carousel gear through a first axle shaft, wherein the at least one sample holder cassette has a first degree of rotation about the first axle shaft;
a first planet drive gear underlying and vertically coupled to the carousel gear through a second axle shaft that extends from the carousel gear through the first planet drive gear, wherein the carousel gear and the at least one sample holder cassette each have a second degree of rotation about the second axle shaft that is independent of the first degree of rotation; and
at least one planet gear that is laterally connected to a second planet drive gear, and is interposed between each of the carousel gear and the first planet drive gear, wherein each of the at least one planet gear and the second planet drive gear selectively define the first degree of rotation, without affecting the second degree of rotation of the carousel gear.

2. The cryogenic sample positioning system of claim 1, wherein the at least one planet gear is vertically coupled to the at least one sample holder cassette through the first axle shaft, wherein the at least one planet gear is isolated from the underlying first planet drive gear.

3. The cryogenic sample positioning system of claim 1, wherein the first and the second planet drive gears are rigidly connected to each other, and are connected to the carousel gear through the second axle shaft, the first and the second planet drive gear being co-axially rotatable about the second axle shaft independent of the rotation of the carousel gear.

4. The cryogenic sample positioning system of claim 1, wherein the at least one planet gear is rotatable by the first planet drive gear through the second planet drive gear, wherein the rotation of each of the first planet drive gear, the at least one planet gear and the second planet drive gear facilitates defining the rotation of the at least one sample holder cassette about the first axle shaft.

5. The cryogenic sample positioning system of claim 1, further comprising a bushing adjoining the second axle shaft, wherein the bushing laterally separates the carousel gear, and the first and the second planet drive gears from the second axle shaft, the bushing comprising a material that has a thermal coefficient of expansion substantially equal to that of stainless steel.

6. The cryogenic sample positioning system of claim 1, further comprising a first pinion gear laterally coupled to the first planet drive gear, and a second pinion gear laterally coupled to the carousel gear, wherein each of the first pinion gear and the second pinion gear are configured to discretely rotate each of the carousel gear and the first planet drive gear.

7. The cryogenic sample positioning system of claim 6, further comprising a first pinion shaft that is attached to the first pinion gear, wherein rotation of the first pinion shaft and the first pinion gear define rotation of the at least one planet gear and the corresponding sample holder cassette of the at least one sample holder cassette about the first axle shaft.

8. The cryogenic sample positioning system of claim 6, further comprising a second pinion shaft that is attached to the second pinion gear, wherein rotation of the second pinion shaft and the second pinion gear define rotation of the carousel gear that is independent of the rotation of the underlying first and the second planet drive gears.

9. The cryogenic sample positioning system of claim 1, wherein the at least one planet gear has a diameter that is less than a diameter of the carousel gear.

10. The cryogenic sample positioning system of claim 1, wherein the cryogenic sample positioning system is enclosed in a cryogenic chamber having an opening, wherein the at least one opening of the at least one sample holder cassette is directly aligned with the opening of the cryogenic chamber so as to accurately position a sample within the at least one opening.

11. A method, comprising:
providing a cryogenic sample positioning structure, comprising:
at least one sample holder cassette comprising at least one opening that is vertically coupled to an upper surface of a carousel gear through a first axle shaft, wherein the at least one sample holder cassette has a first degree of rotation about the first axle shaft;
a first planet drive gear underlying and vertically coupled to the carousel gear through a second axle shaft that extends from the carousel gear through the first planet drive gear, wherein the carousel gear and the at least one sample holder cassette each have a second degree of rotation about the second axle shaft that is independent of the first degree of rotation; and
at least one planet gear that is laterally connected to a second planet drive gear, and is interposed between each of the carousel gear and the first planet drive gear, wherein each of the at least one planet gear and the second planet drive gear selectively define the first degree of rotation, without affecting the second degree of rotation of the carousel gear; and
disposing the cryogenic sample positioning structure within a cryogenic chamber having an opening, wherein the at least one opening of the at least one sample holder cassette is directly aligned with the opening of the cryogenic chamber so as to accurately position a sample within the at least one opening.

12. The method of claim 11, wherein the step of providing comprises providing the at least one planet gear that is vertically coupled to the at least one sample holder cassette through the first axle shaft, wherein the at least one planet gear is isolated from the first planet drive gear.

13. The method of claim 11, wherein the first and the second planet drive gears are rigidly connected to each other, and are connected to the carousel gear through the second axle shaft, the first and the second planet drive gear being co-axially rotatable about the second axle shaft independent of the rotation of the carousel gear.

14. The method of claim 11, wherein the at least one planet gear is rotatable by the first planet drive gear through the second planet drive gear, wherein the rotation of each of the first planet drive gear, the at least one planet gear, and the second planet drive gear facilitates defining the rotation of the at least one sample holder cassette about the first axle shaft.

15. The method of claim 11, further comprising providing a first pinion gear that is laterally coupled to the first planet drive gear, and a second pinion gear that is laterally coupled to the carousel gear, wherein each of the first pinion gear and the second pinion gear are configured to discretely rotate each of the carousel gear and the first planet drive gear.

16. The method of claim 15, further comprising providing a first pinion shaft that is attached to the first pinion gear, wherein rotation of the first pinion shaft and the first pinion gear define rotation of the at least one planet gear and the corresponding sample holder cassette of the at least one sample holder cassette about the first axle shaft.

17. The method of claim 15, further comprising providing a second pinion shaft that is attached to the second pinion gear, wherein rotation of the second pinion shaft and the second pinion gear define rotation of the carousel gear that is independent of the rotation of the underlying first and the second planet drive gears.

18. The method of claim 11, further comprises providing a bushing adjoining the second axle shaft, wherein the bushing laterally separates the carousel gear, and the first and the second planet drive gears from the second axle shaft, the bushing comprising a material that a thermal expansion of coefficient substantially equal to that of stainless steel.

19. The method of claim 11, wherein the at least one planet gear has a diameter that is less than a diameter of the carousel gear.

20. The method of claim 11, further comprising providing a fiber-optic sensor within the cryogenic chamber, the fiber-optic sensor facilitating determining positioning of the at least one sample holder cassette relative to that of the opening of the cryogenic chamber.

* * * * *